US00PP17305P2

(12) United States Plant Patent
Carruth

(10) Patent No.: US PP17,305 P2
(45) Date of Patent: Dec. 26, 2006

(54) GRANDIFLORA ROSE PLANT NAMED 'WEKOSUPALZ'

(50) Latin Name: *Rosa hybrida*
Varietal Denomination: WEKosupalz

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 3 days.

(21) Appl. No.: 11/230,960

(22) Filed: Sep. 19, 2005

(51) Int. Cl.
*A01H 5/00* (2006.01)

(52) U.S. Cl. ..... Plt./132
(58) Field of Classification Search ..... Plt./132, Plt./130
See application file for complete search history.

*Primary Examiner*—Kent Bell
*Assistant Examiner*—June Hwu
(74) *Attorney, Agent, or Firm*—Christie, Parker & Hale, LLP

(57) ABSTRACT

A new variety of Grandiflora rose suitable for garden decoration, having flowers of golden orange coloration with a bronzy red reverse.

1 Drawing Sheet

Classification: The present invention relates to a new *Rosa hybrida* plant.

Variety denomination: The new plant has the varietal denomination 'WEKosupalz'.

BACKGROUND OF THE INVENTION

This invention relates to a new and distinct variety of Grandiflora Rose. It has as its seed parent an undisseminated seedling of my creation with the following genetic origin ['O Sole Mio'×('Katherine Loker'×'Gingersnap' (U.S. Plant Pat. No. 4,330))]. X unknown and as its pollen parent the variety known as 'WEKpaltlez' (U.S. Plant Pat. No. 15,155).

SUMMARY OF THE INVENTION

Among the features which distinguish the new variety from other presently available and commercial rose cultivars known to the inventor are the following combination of characteristics: its predominantly smooth peduncle with numerous hairs, its numerous hairs on the style, its flowers of golden orange coloration with a bronzy red reverse, its very vigorous and very upright habit. The plant has a very upright growing habit, suitable for outoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKosupalz' may be asexually propagated by cuttings, budding and grafting. The budding and grafting successfully occurred on the plant/rootstock *Rosa hybrida* 'Dr. Huey'.

COMPARISON WITH PARENTS

The new rose may be distinguished from its seed parent, an undisseminated seedling of my creation by the following combination of characteristics: whereas 'WEKosupalz' bears flowers of golden orange coloration with a bronzy red reverse and with double petalage (about 26 to 30 petals), the undisseminated seedling bears flowers of pure yellow coloration with significantly heavier petalage(about 38 to 45 petals). The undisseminated seedling bears light green foliage, whereas the new variety bears significantly darker foliage.

The new variety may be distinguished from its pollen parent, 'WEKpaltlez' by the following combination of characeristics: whereas 'WEKosupalz' bears large sized flowers (about 10.0 to about 13.1 cm. in diameter) of golden orange coloration with a bronzy red reverse and with double petalage (about 26 to 30 petals), 'WEKpaltlez' bears significantly smaller flowers (about 6.7 to about 10.2 cm in diameter) of unusual smoky chocolate orange coloration overlaid with a wash of lavender with lesser petalage (about 17 to 27 petals). The new variety bears almost matte to slightly glossy dark green foliage, whereas the pollen parent bears very glossy dark green foliage.

COMPARISON WITH THE CLOSEST COMMERCIALLY AVAILABLE CULTIVAR

The new variety may be distinguished from its closest commercially available cultivar, 'CHRISGOBRO' by the following combination of characteristics: whereas 'WEKOSUPALZ' bears flowers with double petalage (about 26 to 30 petals), 'CHRISGOBRO' bears flowers with significantly lesser petalage (about 17 to 25 petals). The new variety has a very upright tall growing habit (about 170 to about 200 cm. In height) with very vigorous growth, whereas 'CHRISGOBRO' has an upright moderately speading growth habit with significantly smaller mature growth habit and of lesser vigor.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or value are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of April. Phenotypic expression may vary with environmental, cultural and climatic conditions, as well as differences in conditions of light and soil.

FLOWER

The new variety sometimes bears its flowers singly, sometimes in clusters of two to five or more per stem. Flowers may be borne in somewhat irregular rounded clusters on strong long stems (about 52 to about 86 cm.). Outdoors, the plant blooms abundantly and nearly continuously during the growing season. The flowers have a moderate fruity to apple-like fragrance.

BUD

The peduncle is about 3.6 to about 6.3 cm. in length, of somewhat heavy caliper (about 0.3 to about 0.5 cm. in diameter), and usually erect and somewhat stiff. It is predominantly smooth, without any stipitate glands but with numerous hairs. Peduncle color is between 144A and 148A often heavily suffused, especially on the side exposed to the sun, with between 183A and 187B.

Before the calyx breaks, the bud is about 1.0 to about 1.9 cm. in diameter at the widest point, about 1.3 to about 2.5 cm. in length, and very pointed to somewhat ovoid in shape with a conspicuous neck. The surface of the bud bears few foliaceous appendages, many hairs and very few stipitate glands, usually with slender entire foliaceous parts extending beyond the tip of the bud about ½ or more of its length. Bud color is between 144A and 138A often heavily suffused, especially on the side exposed to the sun, with between 183A and 187A.

The sepals are about 2.8 to about 4.3 cm, in length and about 0.6 to about 1.1 cm. in width at the widest point. The outer surface color of the sepal is between 144A and 138A often heavily suffused, especially on the side exposed to the sun, with between 183A and 187A. The inner surface color of the sepal is between 137C and 138B and covered with fine wooly tomentum; sepal margins are lined with very few stipitate glands and numerous hairs. Most of the stipitate glands are on the edge of the foliaceaous appendages.

The receptacle of the flower is of somewhat short length (about 0.5 to about 0.7 cm.) and small in caliper (about 0.6 to about 0.8 cm. in diameter). The receptacle is globular to almost rounded in form. It surface is very smooth with thick fleshy walls. The receptacle color is between 144A and 138A.

As the petals open (after the calyx breaks), the bud is about 2.1 to about 2.8 cm. in diameter at the widest point, about 3.7 to about 4.1 cm. in length, and pointed to moderately ovoid in form. The color of the under surfaces of the newly opened petals is between 45C and 60C. At the point where the petal attaches, there is a small zone of between 4B and 6C. The color of the upper surfaces of the newly opened petals is between 20A and 16C. There is no visible change in coloration at the point where the petal attaches.

BLOOM

When fully open, the bloom ranges from about 10.0 to about 13.1 cm. in diameter. Petalage is double with about 26 to 30 petals and about 6 to 8 petaloids irregularly arranged. When partially open, the bloom form is somewhat globular to cupped, and the petals are moderately tightly spiraled to cupped with petal edges somewhat reflexed outward. When fully open, the bloom form is more cupped, and the petals are loosely cupped with petal edges somewhat reflexed outward.

PETALS

The substance of the petals is moderately heavy and of medium thickness, with upper surfaces moderately satiny and under surfaces slightly shiny to matte. The outer petals are nearly rounded to somewhat obovate in shape with mostly mucronate and sometimes rounded apices. The inner petals are moderately obovate in shape with mostly mucronate and sometimes rounded apices. The petals are about 4.4 to about 6.6 cm. in length and about 4.1 to about 6.5 cm. in width at the widest point. Petal margins are entire. Petaloids are about 1.6 to about 2.4 cm. in length and about 0.6 to about 0.9 cm. in width at the widest point. Petaloids are shaped moderately oblanceolate to somewhat oblong with rounded apices.

NEWLY OPENED FLOWER

The under surface color of the outer petals is between 47C and 185D often blushed with between 60A and 60B. At the point where the petal attaches, there is a small zone of between 4B and 6C. The upper surface color of the outer petals is between 14C and 14D fading slightly toward the petal edge to between 19C and 14D. There is no visible change in coloration at the point where the petal attaches.

The under surface color of the intermediate and inner petals is between 35B and 185D. The upper surface color of the intermediate and inner petals is between 14C and 14D.

The under and upper surface color of the petaloids are similar in coloration to the upper and under surfaces of the intermediate and inner petals.

The general tonality of the newly opened flower is between 14C and 14D with a reverse petals color of between 35B and 185D.

THREE-DAY-OLD FLOWER

The under surface color of the outer petals is between 50B and 54C often blushed with between 60A and 61B. At the point where the petal attaches, there is a small zone of between 4B and 6C. The upper surface color of the outer petals is between 19C and 14D often lightly blushed toward the petals edge with between 184D and 59D. There is no visible change in coloration at the point where the petal attaches.

The under surface color of the intermediate and inner petals is between 43D and 54C. The upper surface color of the intermediate and inner petals is between 19C and 14D often lightly blushed toward the petals edge with between 184D and 59D.

The under and upper surface color of the petaloids are similar in coloration to the upper and under surfaces of the intermediate and inner petals.

The general tonality of the three-day-old flower is between 19C and 14D often lightly blushed toward the petals edge with between 184D and 59D and with a reverse petals color of 43D and 54C.

On the spent bloom, the petals usually drop off cleanly.

In April in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids or tucked in the calyx. The filaments are of moderately long length (about 0.5 to about 1.2 cm.), most with anthers. Filaments are between 13B and 12A in color. The anthers are of medium size for the class and all open approximately at the same time. Anther color is between 23B and 12C when immature and between 200A and 167B at maturity. Pollen is abundant and between 17C and 15B in color.

FEMALE REPRODUCTIVE ORGANS

Pistils vary in number (average about 90). The styles are moderately uneven, long in length (about 0.5 to about 1.1 cm.), somewhat thin in caliper, and moderately separated to loosely bunched. Stigma color is between 13C and 12B. Style color is between 1D and 150D usually heavily suffused near the top with between 53B and 53C. The styles are usually covered with numerous hairs. Ovaris are usually all enclosed in the calyx.

Hips have not been observed on this variety when grown in Upland, Calif.

FOLIAGE

The compound leaves are usually comprised of three to seven leaflets and are borne abundantly. The seven-leaflet leaves are about 12.7 to about 15.8 cm. in length and about 10.5 to about 12.8 cm. in width at the widest point, crisp to moderately leathery in texture, and almost matte to slightly glossy in finish. The terminal leaflets are about 5.5 to about 8.2 cm. in length and about 3.2 to about 5.1 cm. in width at the widest point, shaped oval with moderately acuminate apices and acute to somewhat rounded bases. Their margins are usually simply serrate.

The upper surface color of the mature leaf is darker than between 147A and 137A. The under surface color of the mature leaf is between 147B and 138A. The upper surface color of the young leaf is between 144A and 146C, usually heavily suffused with near 187A. The under surface color of the young leaf is between 138B and 147B, usually heavily suffused with near 187A.

The rachis is average in caliper and rough. The upper side is shallowly grooved with many hairs and stipitate glands on the edges of the grooves. The under side of the rachis is rough with few hairs and stipitate glands and few small prickles. The rachis color is between 146C and 146B.

The stipules are about 1.4 to about 1.9 cm. in length and of medium width (about 0.5 to about 0.7 cm.) with moderately long straight points that usually turn out at an angle of more than 45 degrees and often recurve toward the stem. The stipules color is between 146C and 146B.

The petiole is average in caliper and rough. It is about 0.7 to about 1.1 cm. in length and about 0.1 to about 0.15 cm in diameter at the widest point. The upper side is shallowly grooved with many hairs and stipitate glands on the edges of the grooves. The under side of the petiole is rough with few hairs and stipitate glands and few small prickles. The petiole color is between 146C and 146B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a very upright tall growing habit (about 170 to about 200 cm. in height and about 92 to about 108 cm. spread at the widest point), with very full branching. It displays very vigorous growth and the canes are of somewhat light to medium caliper for the class.

The color of the major stems is between 148A and 146A. They bear many large prickles that are about 0.6 to about 1.0 cm in length. The large prickles are almost straight and angled slightly downward with a somewhat long narrow oval base; prickle color is near 166D. The major stem bears few small prickles of similar shape and coloration.

The color of the branches is between 146B and 148A. They bear many large prickles which are of similar size and shape to the large prickles on the major stems; prickle color is between 183D and 187B. The branches bear few small prickles of similar shape and coloration.

The color of the new shoots is between 144A and 148B often heavily suffused with between 183A and 187A. They bear many large prickles which are of similar size and shape to the large prickles on the major stems; prickle color is between 183A and 187A. The shoots bear few small prickles of similar shape and coloration.

I claim:

1. A new and distinct Grandiflora rose plant of the variety substantially as described and illustrated herein.

* * * * *

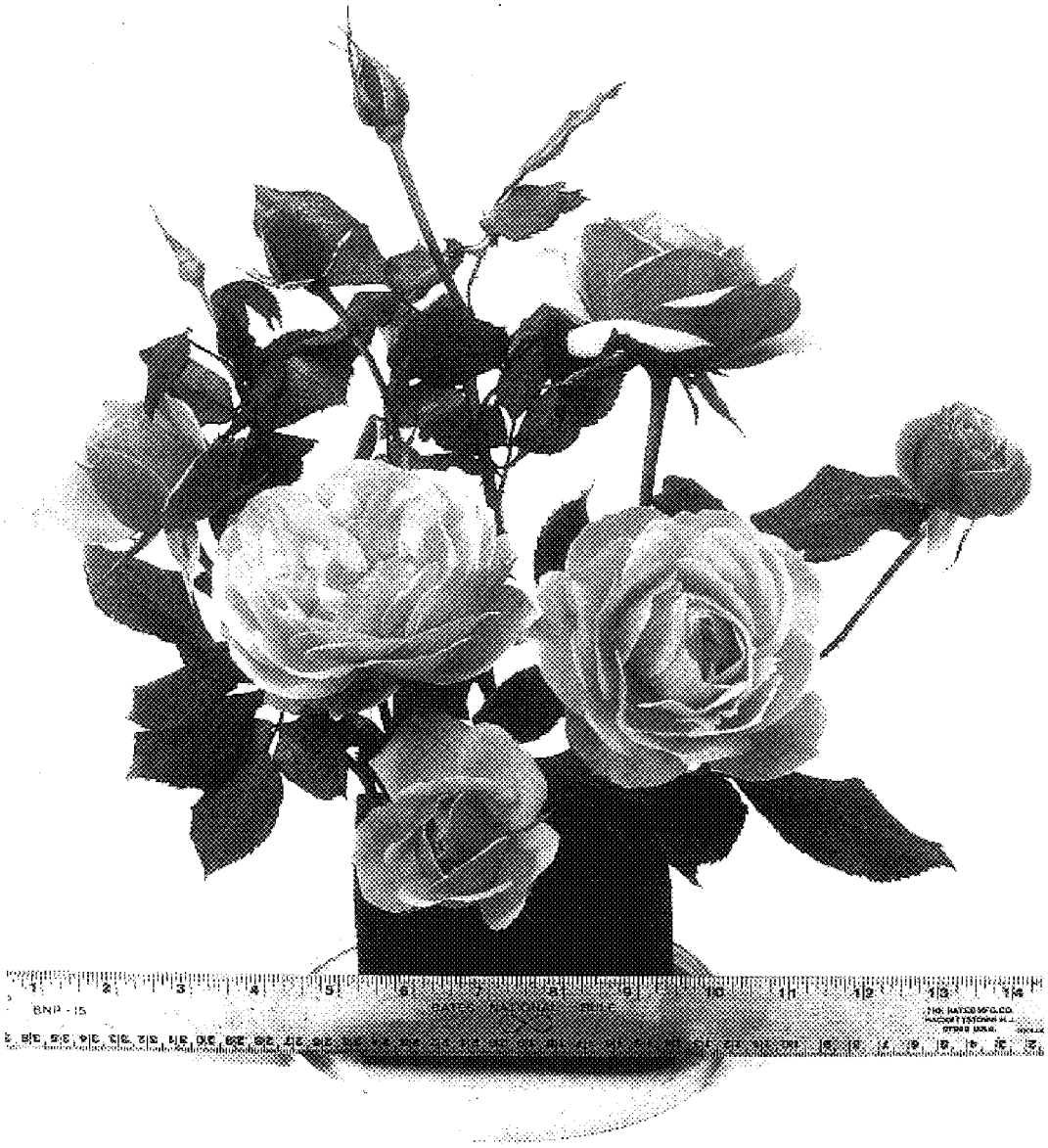
BNP - 15